United States Patent
Jay

(10) Patent No.: US 7,699,058 B1
(45) Date of Patent: Apr. 20, 2010

(54) HAIR TREATMENT METHOD

(76) Inventor: Harvey H. Jay, 14 Cayuga Rd., Scarsdale, NY (US) 10583

( * ) Notice: Subject to any disclaimer, the term of this patent is extended or adjusted under 35 U.S.C. 154(b) by 638 days.

(21) Appl. No.: 11/201,580

(22) Filed: Aug. 11, 2005

Related U.S. Application Data

(63) Continuation-in-part of application No. 10/418,604, filed on Apr. 18, 2003, now Pat. No. 7,175,617, which is a continuation-in-part of application No. 10/291,086, filed on Nov. 8, 2002, now Pat. No. 6,824,542, said application No. 11/201,580 is a continuation-in-part of application No. 10/773,621, filed on Feb. 6, 2004, now Pat. No. 7,217,267, which is a continuation-in-part of application No. 10/647,948, filed on Aug. 26, 2003.

(51) Int. Cl.
*A61B 19/00* (2006.01)
*A61B 18/18* (2006.01)

(52) U.S. Cl. .......................... 128/898; 606/9

(58) Field of Classification Search ...... 606/3, 606/9; 607/88–91; 128/898
See application file for complete search history.

(56) References Cited

U.S. PATENT DOCUMENTS

| | | | |
|---|---|---|---|
| 3,713,453 A * | 1/1973 | Chiaro et al. ............... 132/212 |
| 4,819,669 A | 4/1989 | Politzer |
| 5,425,728 A | 6/1995 | Tankovich |
| 5,533,266 A * | 7/1996 | Kelman ...................... 30/122 |
| 5,595,568 A | 1/1997 | Anderson et al. |
| 5,606,798 A | 3/1997 | Kelman |
| 5,683,380 A | 11/1997 | Eckhouse et al. |
| 5,707,403 A | 1/1998 | Grove et al. |
| 5,735,844 A * | 4/1998 | Anderson et al. ............... 606/9 |
| 5,849,029 A | 12/1998 | Eckhouse et al. |
| 5,885,273 A | 3/1999 | Eckhouse et al. |
| 5,895,568 A | 4/1999 | Koltunov |
| 5,993,440 A | 11/1999 | Ghassemi |
| 6,050,990 A * | 4/2000 | Tankovich et al. ............. 606/9 |
| 6,063,076 A | 5/2000 | Mehl, Sr. et al. |
| 6,152,917 A | 11/2000 | Tankovich |
| 6,162,211 A | 12/2000 | Tankovich et al. |
| 6,162,212 A | 12/2000 | Kreindel et al. |
| 6,174,325 B1 | 1/2001 | Eckhouse et al. |
| 6,187,001 B1 * | 2/2001 | Azar et al. .................... 606/9 |
| 6,228,074 B1 * | 5/2001 | Almeida ...................... 606/9 |
| 6,267,771 B1 | 7/2001 | Tankovich et al. |
| 6,280,438 B1 | 8/2001 | Eckhouse et al. |
| 6,306,160 B1 | 10/2001 | Nidetzky |
| 6,383,176 B1 | 5/2002 | Connors et al. |
| 6,387,089 B1 | 5/2002 | Kreindel et al. |
| 6,406,474 B1 | 6/2002 | Neuberger et al. |
| 6,514,243 B1 | 2/2003 | Eckhouse et al. |
| 6,663,659 B2 * | 12/2003 | McDaniel ................... 607/88 |
| 6,676,655 B2 | 1/2004 | McDaniel |
| 6,824,542 B2 * | 11/2004 | Jay ............................... 606/9 |
| 6,916,316 B2 * | 7/2005 | Jay ............................... 606/9 |
| 7,175,617 B2 * | 2/2007 | Jay ............................... 606/9 |
| 7,201,764 B2 * | 4/2007 | Pearl et al. .................. 607/88 |
| 7,217,267 B2 * | 5/2007 | Jay ............................. 606/18 |
| 2003/0055414 A1 | 3/2003 | Altshuler et al. |
| 2003/0167033 A1 | 9/2003 | Chen et al. |
| 2004/0230260 A1 | 11/2004 | MacFarland et al. |
| 2006/0142741 A1 * | 6/2006 | Jay ............................... 606/3 |

* cited by examiner

*Primary Examiner*—Ahmed M Farah
(74) *Attorney, Agent, or Firm*—R. Neil Sudol; Henry D. Coleman; William J. Sapone

(57) ABSTRACT

A method for hair styling includes generating a pulses of light having a predetermined electromagnetic spectrum with one or more wavelengths absorbable by hair and directing the pulses of light towards hair fibers of an individual. The pulses have at least one pulse duration and a total energy all predetermined to effectively vary a characteristic of the hair fibers owing to absorption of light of the pulses by the hair fibers. By virtue of the directing of the pulses of light towards the hair fibers and absorption of light of the pulses by the hair fibers, at least one selected characteristic of the hair fibers is changed, the one selected characteristic being hair curvature, hair fiber thickness, or hair length.

9 Claims, 1 Drawing Sheet

HAIR TREATMENT METHOD

CROSS-REFERENCE TO RELATED APPLICATION

This application is a continuation-in-part of application Ser. No. 10/418,604 filed Apr. 18, 2003, now U.S. Pat. No. 7,175,617, which in turn is a continuation-in-part of application Ser. No. 10/291,086 filed Nov. 8, 2002, now U.S. Pat. No. 6,824,542. This application is also a continuation-in-part of application Ser. No. 10/773,621 filed Feb. 6, 2004, which in turn is a continuation-in-part of application Ser. No. 10/647,948 filed Aug. 26, 2003.

BACKGROUND OF THE INVENTION

This invention relates generally to a hair treatment process. More particularly, this invention relates to a method for the use of pulsed light energy to treat hair.

As discussed in U.S. Pat. No. 6,280,438, hair may be removed from selected skin surfaces by the application of intense, wide area, pulsed electromagnetic (light) energy. According to the methodology of U.S. Pat. No. 6,280,438, the energy heats the hair and coagulates the tissue around the hair and follicle without damaging the healthy skin. Pursuant to that prior art disclosure, it is preferable to provide an optically transparent water based gel on the skin prior to treatment with the electromagnetic energy. The gel cools the epidermis but is applied so as not to enter the cavity around the hair follicle, and thus does not cool the hair and the hair follicle. The applied energy then coagulates the hair without damaging the skin.

U.S. Pat. No. 6,280,438 teaches the use of incoherent polychromatic radiation in a wavelength range that penetrates into the skin without being highly attenuated. It is indicated in the patent that wavelengths shorter than 550 nm are not useful because they will be highly attenuated before reaching the lower parts of the hair follicles. Instead, wavelengths in the range of 550 to 630 nm are heavily absorbed by blood and can therefore be used to coagulate the vessels that feed the hairs. Additionally, longer wavelengths, in the range of 600 to 1100 nm have a very good penetration into non-pigmented skin and can be used to couple to the melanin of the hair.

U.S. Pat. No. 5,885,273 discloses a method of removing hair that includes producing a plurality of pulses of incoherent electromagnetic energy, which is filtered in accordance with the color of the hair being removed. A flashlamp produces pulses having delays on the order of 0.1 msec to 100 msec, and an energy fluence on the order of 10 to 100 $J/cm^2$. Energy that has a wavelength of less than 500 nm or 600 nm and greater than 1300 nm is preferably filtered out. Light is applied to the treated area in either a long pulse or in a sequence of pulses separated by a delay. The delay and/or pulse length is preferably controlled by the operator to provide enough heat to remove the hair but not enough heat to damage the skin. For example, the pulse length or delay between the pulses should be more than the cooling time of the gel covered epidermis and less than the cooling time of the hair and follicle. Specifically, a pulse length of 50 msec if a single pulse is used or a delay of 50 msec between the pulses if a pulse sequence is used are appropriate values.

In brief, the art using electromagnetic radiation such as pulses of incoherent light is intended to permanently remove hair from selected skin surfaces. The light pulses have parameters such as spectral dispersion, pulse duration and total energy that are selected to destroy the hair follicles in the selected skin area. Understandably, such methods carry a certain amount of risk that the skin may be damaged. Accordingly, the prior art methods of hair depilation are typically intended for use by trained cosmetologists and other professionals. The consuming public is left with few options in removing undesired hair.

OBJECTS OF THE INVENTION

An object of the present invention is to provide a method that uses pulsed light energy (electromagnetic radiation) for treating hair.

It is a related object of the present invention to provide a method that uses pulsed light energy (electromagnetic radiation) for temporarily affecting characteristics of a person's hair.

A more particular object of the present invention is to provide such a method of hair treatment that is safe for home use.

It is a related object of the invention to provide a method for hair treatment, which may replace current home-based methods, for instance, of treating hair.

These and other objects of the present invention will be apparent from the drawings and descriptions herein. It is to be understood that each object of the invention is achieved by at least one embodiment of the invention. It is not necessarily the case that any embodiment achieves all of the objects of the invention.

SUMMARY OF THE INVENTION

A method for hair treatment comprises, in accordance with the present invention, generating a predetermined number of pulses of light each having a predetermined electromagnetic spectrum with one or more wavelengths absorbable by hair and directing the pulses of light towards hair fibers of an individual, where the pulses have at least one pulse duration and a total energy all predetermined to effectively vary a characteristic of the hair fibers owing to absorption of light of the pulses by the hair fibers. By virtue of the directing of the pulses of light towards the hair fibers and absorption of light of the pulses by the hair fibers, at least one selected characteristic of the hair fibers is changed, the one selected characteristic being hair curvature, hair fiber thickness, or hair length.

Where the one selected characteristic is hair curvature or hair length, the method may further comprise applying a light-absorbing composition to the hair fibers prior to the directing of the pulses of light towards the hair fibers. The light-absorbing composition is exemplarily water, a gel, or a dye. The light-absorbing composition may be applied uniformly to the hair fibers. In that case, the pulses of light are directed differentially to different sides of the hair fibers. Alternatively, the light-absorbing composition may be applied differentially to different sides of the hair fibers. In that case, the pulses of light need not be applied differentially to different sides of the hair fibers.

Where the one selected characteristic is hair length, the pulses of light may be directed towards end segments of individual hair fibers. This procedure may be used merely to eliminate split ends, in which case any hair shortening is incidental. Alternatively, the procedure may be used to significantly or noticeably shorten hair length. In either case, one may automatically detect free ends of the hair fibers and direct the pulses of light towards the hair fibers at a given distance from the free ends of the hair fibers.

Where the one selected characteristic is hair fiber thickness, the pulses of light may be directed more or less continuously along the lengths of the hair fibers, to thereby split the hair fibers longitudinally, thereby increasing the numbers of the hair fibers and reducing fiber thickness.

Alternatively, where the one selected characteristic is hair fiber thickness, the method may further comprise applying a light-activated adhesive composition to the hair fibers. The light is applied along at least a portion of the lengths of the hair fibers after the applying of the light-activated adhesive composition to the hair fibers, to activate the adhesive composition and thereby fuse some hair fiber sections to other hair fiber sections longitudinally, thereby decreasing the number of the hair fiber sections and increasing fiber thickness along at least a portion of the hair fiber lengths. This procedure may be used to repair split ends.

A hair treatment method comprises, in accordance with the present invention, generating electromagnetic radiation having a predetermined spectral composition and a predetermined intensity in a predetermined number of light pulses each having a predetermined duration collectively having a predetermined total energy and directing the light pulses towards hair fibers protruding from a skin surface so that the generated light pulses are absorbed by the hair fibers, above or outside of a person's skin, to thereby affect a characteristic of the hair fibers.

The light pulses preferably have at least one pulse duration and a total energy all predetermined to effectively vary the characteristic owing to absorption of light of the pulses by the hair fibers, the characteristic being taken from the group consisting of hair curvature, hair fiber thickness, and hair length.

Pursuant to another feature of the present invention, the light pulses are typically directed away from the skin surface from which the hair fibers protrude, so that light of the pulses does not fall on that skin surface. Inasmuch as the present method is directed to the styling of a person's hair, generally head hair, it is typically not desired to completely remove any of the hair fibers, for instance, by severing the hair below the skin line. However, there may be certain hair styles that combine a removal of hair fibers from selected parts of the head in order to effectuate a desired hair growth pattern, together with variations in hair curvature and hair length.

It should be understood that the present methodology may be used in professional settings, in hair dressing salons, by professional hair stylists. Higher energies may be used in such settings.

DETAILED DESCRIPTION

Figure 1:
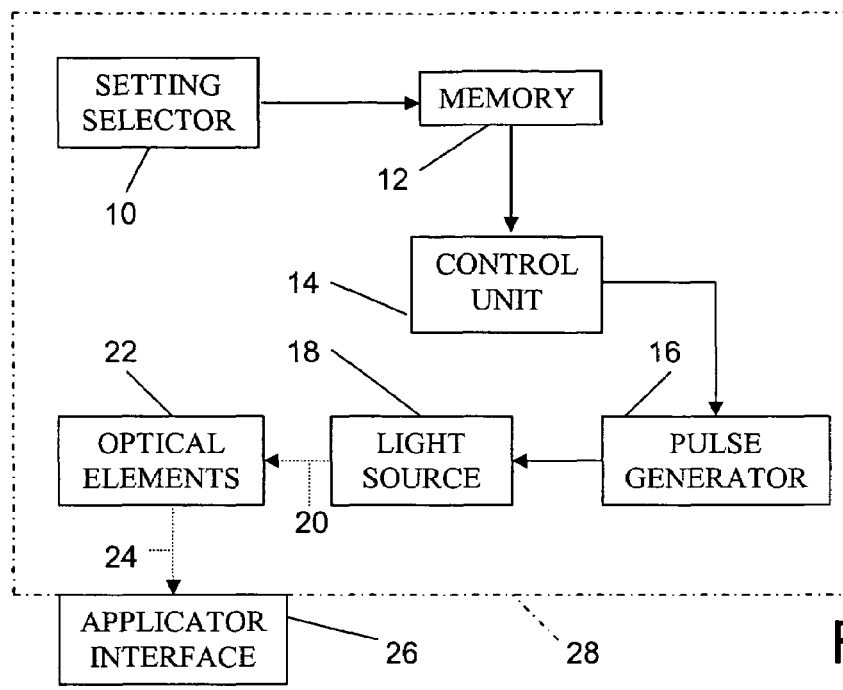
FIG. 1 is a block diagram of a light-pulse generating device for use in a method in accordance with the present invention.

As depicted in FIG. 1, a device for generating light pulses for application to a person's hair in a hair styling process includes a manually operable setting selector 10 connected at an output to a memory 12 in turn connected at an output to a control unit 14. Memory 12 stores pre-established combinations of light pulse parameters including pulse width or duration, inter-pulse interval or delay time, pulse number, light intensity, and total treatment energy. Control unit 14 may be a microprocessor or a special logic circuit connected to a pulse generator 16 for inducing the generator to produce a sequence of electrical control pulses fed to a source 18 of incoherent light energy. Source 18 produces light with a spectral distribution including wavelengths between 200 nm and 1200 nm, for absorption by melanin in the hair fibers or by a dye applied to the hair fibers. Alternatively, the light of the pulses includes a range of wavelengths longer than about approximately 750 nm, for instance, in a range of 800 nm to 1500 nm. Light of this spectral range is absorbed by water in the hair fibers. Control unit 14 may be connected directly to source 18 where the source incorporates means for varying pulse parameters pursuant to encoded instructions from the control unit.

Light source 18 (as well as the entire light pulse applicator) may take any known form such as those disclosed in U.S. Pat. No. 6,280,438 and U.S. Pat. No. 5,885,273. Thus, light source 18 may be a Xenon flashlamp.

Light 20 generated by source 18 is directed through an array of optical elements 22 that may include one or more reflectors, lenses, and filters (not separately shown). Where an adjustable filter is included, control unit 14 may be connected to the filter for operatively modifying the action thereof. For instance, in the case of an adjustable neutral density filter, control unit 14 may induce a change in the filter density to control the intensity, and therefore the power, of the light applied to a selected hair fiber or group of hair fibers.

In the case of multiple wavelengths of light being produced, an adjustable filter may be included in the optical elements 22 and/or an applicator interface 26, which may take the form of a cartridge removably attachable to a casing 28 of the light pulse generating device. These filters can block undesired wavelengths and allow desired wavelengths to pass. Low end filters that block lower or shorter wavelengths, high end filters that block higher or longer wavelengths or band pass filters that block some high or some low end wavelengths may be utilized.

Light 24 leaving the optical array 22 is delivered or applied to hair fibers at selected locations along the hair fibers, and above or outside the skin, via an applicator or interface element 26 exemplarily taking the form of a crystal with one or more slots for the reception of the hair fibers. Applicator or interface element 26 may take the form of a comb with light exit apertures located between adjacent tines, at the base of the tines. Applicator or interface element 26 may additionally or alternatively be composed at least in part of plastic or polymeric material or a liquid such as an aqueous solution. The applicator or interface element 26 may be spaced from the target hair fibers, that is, not in direct contact with the hair, the light pulses being transmitted through the air.

The elements of FIG. 1 are encased in or mounted to a housing 28 of a size and configuration enabling the pulse generation device to be hand held and easily manipulated for purposes of optically treating the head hair of the individual user.

The device of FIG. 1 is preprogrammed to produce light pulses in any of several settings, each setting being defined by a respective combination of particular operational parameters including pulse duration, inter-pulse interval, pulse number, and intensity or total energy. For instance, the device may have a plurality of settings, for instance, high, medium, and low, which vary in the number of applied pulses (e.g., 3, 2, 1), the pulse duration (9 msec, 7 msec, 5 msec), the inter-pulse interval (250 msec, 300 msec, 350 msec), and/or the total energy applied (35 J/cm$^2$, 20 J/cm$^2$, 10 J/cm$^2$, 1 J/cm$^2$, 1 µJ/cm$^2$). A user could start with a low setting to see whether a desired styling effect is attained and if not, try the next higher setting. Usually, it is preferable to use the lowest setting which accomplishes the desired result.

The desired results include changing the hair length, the hair curvature or the thickness of the hair fibers. Cutting the hair generally requires parameter settings that apply pulsed light energy to the hair at a high rate and to a concise or restricted location along the hair fibers. Varying the hair curvature to create or remove waves or curls generally requires parameter settings that apply pulsed light energy to the hair fibers at lower rates and to larger sections of the hair fibers. Changing the thickness of individual fibers typically entails the application of a highly focused or narrow beam of light to the hair fibers along the lengths thereof. Where the desired result is to thin the hair fibers and increase the numbers of hairs, the delivered energy is sufficiently intense to sever the hair fibers or shafts along the lengths thereof and is sufficiently focused to avoid severing and shortening the hair fibers. Where the desired result is to increase fiber thickness, a light- and heat-activated composition or adhesive is applied to the hair fibers prior to the application of the light pulses, which need not be finely focused. The adhesive and the light pulses may be applied only to the end portions of the hair fibers, to fuse and repair split ends.

Figure 2:
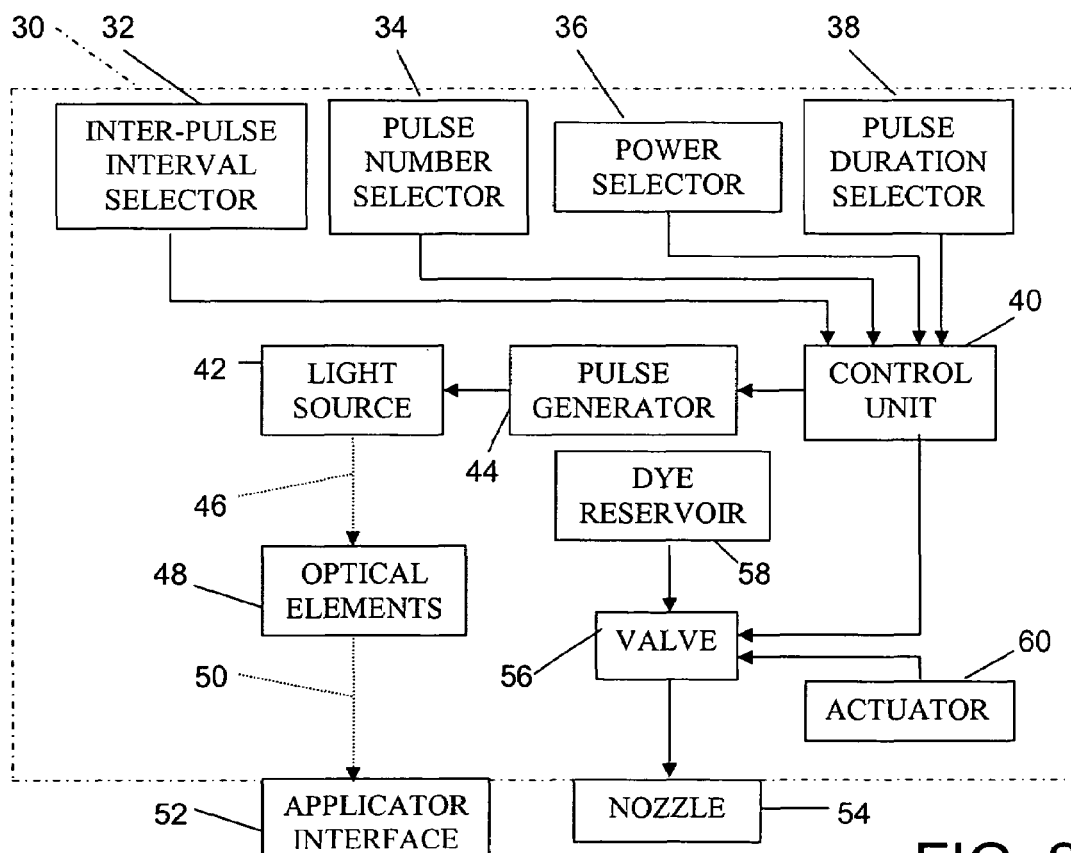
FIG. 2 is a block diagram of another light-pulse generating device for use in a method in accordance with the present invention.

A more advanced or complex device is illustrated in FIG. 2. This device includes a housing 30 having manually actuatable input elements 32, 34, 36, and 38, such as rotary knobs or a solid-state touch screen, which enable a user to individually select multiple operating parameters. Input elements or selectors 32, 34, 36, and 28 are an inter-pulse interval selector, a pulse number selector, a power or energy selector, and a pulse duration selection, respectively. Another selector (not shown) could be for intensity adjustment, while a further selector may be provided for adjusting a light source 42 or a filter in optical elements 48 and/or an applicator 52 for modifying the wavelength band delivered to the target skin surface. Selectors 32, 34, 36, and 38 are operatively tied to a control unit 40 such as a microprocessor or hard-wired log circuit. Control unit 40 regulates the operation of light source 42 such as a conventional flashlamp, either directly or indirectly via a pulse generator 44. Light 46 from source 42 is transmitted along a path through optical elements 48 optionally including one or more reflectors, lenses, and filters (not separately shown). Light 50 at an output of the optical array 48 is applied to a skin surface via applicator or interface element 52.

Applicator or interface element 52 may take the form of a crystal with one or more slots for the reception of the hair fibers. Applicator or interface element 52 may take the form of a comb with light exit apertures located between adjacent tines, at the base of the tines. The latter configuration of applicator or interface element 52 is suitable for cutting, curling (or straightening), and changing hair fiber thickness. Applicator or interface element 52 may additionally or alternatively be composed at least in part of plastic or polymeric material or a liquid such as an aqueous solution. The applicator or interface element 52 may be spaced from the target hair fibers, that is, not in direct contact with the hair, the light pulses being transmitted through the air.

As shown in FIG. 2, the light pulse device may be provided with a fluid dispenser such as a spray nozzle 54 connected to a valve 56 downstream of a pressurized reservoir 58 of a light-absorbing composition. The light-absorbing composition may include pure water, an aqueous solution, a gel, or a dye. In response to an operation of a manual actuator 60 or in response to signals from control unit 40, valve 56 enables a flow of the light-absorbing composition from reservoir 58 to nozzle 54 for application to selected hair fibers. In the case of a dye or gel, the dye or gel is preferably water soluble or removable by soap and water.

In one embodiment of the device of FIG. 2, inter-pulse interval selector 32 provides for intervals in a range from 1 nsec and 2 seconds, whereas pulse number selector 34 is enabled for pulse sequences of one to ten pulses. In addition, power selector 36 permits treatment energies between 1 micro-Joule per square centimeter of hair fibers and 200 Joules per square centimeter, while pulse duration selector 38 enables pulses of 1 nsec to 2 seconds in length. Total pulse sequence duration, from the beginning of the first pulse to the termination of the final pulse, ranges from 1 nsec to 38 seconds. The various pulse sequence parameters may be selectable from sets of discrete values or, alternatively, from continuous ranges.

In the device of FIG. 2, the various parameters are typically not completely independent inasmuch as the total energy selected will function as a constraint on the ranges available for the other parameters, that is, the total energy selected will serve to regulate or circumscribe the ranges available to the user for the other pulse sequence parameters. Where the device of FIG. 2 has no intensity adjustment capability, a selection of the total energy and the pulse duration may determine the number of pulses. Similarly, a selection of the total energy and the number of pulses may determine the pulse duration. If the intensity is an adjustable parameter, once the total energy has been chosen, the user will be able to select the magnitudes of two of the three parameters, pulse duration, intensity and number of pulses. The inter-pulse interval is related to the rate at which radiant energy is applied to hair fibers and may accordingly be subjected to some programmed control. Longer pulse durations and/or delays will deliver energy at a slower rate (total energy is distributed over longer time) and therefore be safer to use with higher energy levels. Preferably, the total energy is always a selectable parameter and is best selected prior to the setting of the other parameters. However, the device of FIG. 2 may be preprogrammed to limit the rate at which radiant energy is applied to hair fibers, which will force restrictions on the user's ability to select pulse parameter values.

In an alternative embodiment of the device of FIG. 2, inter-pulse interval selector 32 enables a selection of intervals ranging from 200 nsec to 2 seconds, while power selector 36 enables treatment energies between 1 $\mu J/cm^2$ and 40 $J/cm^2$. Preferably, the pulse duration and the number of pulses available for selection are restricted so as to prevent the user from delivering energy at too high a rate. Pulse number selector 34 may therefore enable a selection of three to ten pulses per pulse sequence, while pulse duration selector 38 enables a selection of pulses lasting 1 nsec to 2 sec. The various pulse sequence parameters may be selectable from sets of discrete values or, alternatively, from continuous ranges.

A person uses the device of FIG. 1 or 2 to apply pulses of light to hair fibers for purposes of (1) severing hair fibers above the surface of the skin to shorten the hair and/or to remove split ends, (2) modifying the curvature of the hair to create or remove waves or curls in the hair, and/or (3) increasing or decreasing fiber thickness. Pulse parameters may be selected in accordance with the desired styling action. In the case of a largely preprogrammed device (FIG. 1), the user might actuate a keypad or turn selector knobs of setting selector 10 to inform control unit 14 as to whether the desired styling action is cutting, curving or fusing. Also selector 10 may be operated to indicate the user's hair color.

Where reservoir 58, valve 56, actuator 60, and nozzle 54 are provided, the user may be instructed, either by an accompanying brochure or by control unit 14 via a display (not illustrated), that water or a dye or other light-absorbing substance may be introduced into reservoir 58 and dispensed onto the hair via valve 56 and nozzle 54 under the control of actuator 60, in order to provide selected hair segments with enhanced light absorption characteristics. Valve 56, and optionally actuator 60 may be designed to deliver measured amounts of the light-absorbing composition from reservoir 58 onto limited sections of hair fibers. In the case of hair curvature adjustment, the light-absorbing composition may be selectively applied only to certain sections of hair along the length of the hair and to one side of the hair fibers. The light-absorbing composition from reservoir 58 may be applied also to facilitate or enhance hair cutting action, particularly where the user's hair is light in color.

Where it is desired to change hair curvature (waving, curling, straightening), the parameters of the light pulses (incl. duration, inter-pulse interval, total energy) are such that the hair is differentially heated along one side of the hair. The heat is not so great as to sever the hair and is distributed over a region of the hair as selected by the user to produce gentle waves, large or small curls or a straightening effect.

Where it is desired to cut hair, the parameters selected for the light pulses are such that a relatively large amount of light energy is absorbed in a small region of the hair in a relatively short period of time. Thus, the heat is so great that the hair is severed at the point of light application.

In the case of hair splitting, the parameters selected for the light pulses are such that a large amount of light energy is absorbed centrally along the lengths of the hair fibers. Thus, the heat is so great that the hair is split along the line of light application.

The devices of FIGS. 1 and 2 may be provided with a speed sensor disposed in or adjacent to each applicator interface 26 and 52 for detecting the relative speed between the applicator interface, on the one hand, and the hair as it is being drawn through the applicator interface. This sensor is connected to control unit 14 or 40 for enabling that unit to adjust the light parameters to achieve a desired curving or straightening effect. To that end a setting selector (not shown) may be provided for advising control unit 1 or 40 not only that a curvature function is desired, but also the degree of curvature. For instance, the degree of curvature is high where tight curls are desired and low where a gentle wave is desired.

The speed sensor may also be used to facilitate cutting to create a tapered or layered look. Thus, the light pulses may be emitted in packets or bursts at intervals determined in part by the speed of the hair relative to applicator interface 26 or 52.

Where the user desires to increase the thickness of his or her individual hair fibers, reservoir 58 may be filled with a liquid light-activatable adhesive composition. This composition is applied to the hair via nozzle 54. Applicator interface 26 or 52 has a comb configuration where the separation of the tines is such that a plurality of hairs are drawing through the gaps during a hair treatment procedure. A speed sensor is useful in this case also to enable control unit 14 or 40 to vary the applied light in accordance with the rate that the fibers are being drawn through the comb tines.

During a calibration or initialization stage, the user should first select a relatively low-energy pulse sequence to determine whether that sequence is effective in achieving the desired end result, whether that result is cutting, splitting, fusing, curving, or straightening. The individual may find that a given setting does not adequately achieve the desired end result. In such cases, the individual should retry the calibration or initialization procedure using a higher-energy setting.

Using the device of FIG. 1, an individual will first select a low setting to determine whether that low setting is effective. If not, a next higher or medium setting may be tried. Generally, higher settings will be used only as the circumstances warrant, for instance, if the hair fibers are thick and the hair is light. Preferably, however, a dye is applied to the hair to facilitate hair styling. After the styling process, the dye may be removed from the hair.

In determining optimal settings with the device of FIG. 2, a user should choose initial parameter values which in combination result in the application of small amounts of energy. Thus, where one or more selected pulse parameters are associated with high treatment energies, other pulse parameters should be selected that are associated with low treatment energies.

Where all the pulse parameters are independently adjustable, lower treatment energies will generally result from settings involving few pulses (say, 1-3 instead of 8-10 pulses), long inter-pulse intervals (300 msec or more), short pulse durations (20 msec or less), low light intensity (if selectable, for example, via an adjustable neutral density filter), and low total energies (less than 40 Joules per square centimeter of skin surface).

Where the various pulse parameters are not independently selectable, for instance, where the total energy applied is a controlling factor, adjustments made in the parameters for purposes of incrementally enhancing the hair removal effectiveness of the device of FIG. 2 will be different from the case of completely independent parameter values. For instance, once the total applied energy and total pulse sequence time have been selected, decreasing the number of pulses will require an increase in pulse length and/or an increase in pulse intensity in order to deliver the same amount of total energy in the fixed time. These changes will increase the effectiveness of the light application inasmuch as the rate of energy delivery is increased. In contrast, once the total applied energy and total pulse sequence time have been selected, increasing the pulse duration will decrease the instantaneous rate at which energy is applied to the target hair fibers by decreasing the light intensity.

During the calibration or initialization stage using the device of FIG. 1 or FIG. 2, light is used on protruding hair fibers. Light is applied to the hair and may be directed away from the skin of the user or customer and particularly away from the skin surface from which the hair is growing. Combing or brushing may be used to expedite or enhance the styling process.

Different pulse parameter settings are recommended for different grades of hair (different colors, different fiber diameters, different hair densities, different other hair characteristics). For example, different settings will be necessary for the different grades of hair in order to optimize results. In addition, hair characteristics may also vary from one skin area to another.

After the user has determined appropriate settings of the pulse sequence parameters for different styling results, the user then treats each tress of hair with pulsed light at the respective setting.

This hair styling method contemplates, therefore, the application to protruding hair fibers of a pulse sequence having a predetermined number of pulses of light of a predetermined electromagnetic spectrum, a predetermined duration, a predetermined inter-pulse interval, and a predetermined total energy. These pulse sequence parameters are determined in part by the design of the light generating device used and in part by the selections made by the user.

The light of the pulses is generally incoherent and the spectrum includes but is not limited to wavelengths between about 200 nm and 1200 nm. This spectral range targets melanin in the hair fibers, as well as any dyes applied to the fibers.

In addition, wavelengths above 800 nm (e.g. between 800 nm and 1500 nm) will target water molecules in the hair. However, single wavelengths of laser or coherent light may be delivered at one time, when desired.

In other embodiments of a light generation and application device, one or more of the pulse parameters may vary during a single treatment session. For instance, the inter-pulse interval or the pulse duration may increase or decrease from the beginning of a pulse sequence to the end of the pulse sequence. The resulting instantaneous rate of energy application may therefore vary during the pulse sequence.

Listed below are a number of exemplary settings or combinations of operational parameters particularly suitable for home-use and attainable with either the device of FIG. 1 having pre-established settings or parameter combinations or the device of FIG. 2 where the various pulse sequence parameters may be individually adjusted independently of the other parameters. In these examples, the total times of the pulse sequences are determined by the selected numbers of pulses, the selected pulse durations and the selected inter-pulse intervals. The light intensity may be automatically adjusted by the light generating device if necessary to ensure consistency among the listed parameter settings.

Home Use Example 1

In a preferred setting or combination of operational parameters suitable for home use, an incoherent light applicator device for cutting hair fibers in a styling process generates pulses with a pulse number of two, a pulse duration of 7 msec, an inter-pulse interval of 300 msec, a total pulse energy of 20 $J/cm^2$, and a spectral distribution of a commercially available flashlamp, including wavelengths between 500 and 1200 nm.

Home Use Example 2

A slightly higher setting or combination of operational parameters for an incoherent light applicator device suitable for home use involves a pulse sequence with a pulse number of two, a pulse duration of 7 msec, an inter-pulse interval of 250 msec, a total pulse energy of 20 $J/cm^2$, and a spectral distribution of a commercially available flashlamp, including wavelengths between 500 and 1200 nm. Although the total amount of energy is the same as in the first example, the shorter interpulse interval means that the rate of energy transmission to the target hair fibers is higher.

Home Use Example 3

A higher setting or combination of operational parameters for an incoherent light applicator device involves pulses with a pulse number of two, a pulse duration of 5 msec, an inter-pulse interval of 250 msec, a total pulse energy of 25 $J/cm^2$, and a spectral distribution of a commercially available flashlamp, including wavelengths between 500 and 1200 nm. In this example, not only is the total energy larger than in the second example, but the rate of energy application is higher owing to the shorter pulse duration.

Home Use Example 4

An even higher setting or combination of operational parameters for an incoherent light applicator device involves pulses with a pulse number of two, a pulse duration of 5 msec, an inter-pulse interval of 210 msec, a total pulse energy of 37 $J/cm^2$, and a spectral distribution of a commercially available flashlamp, including wavelengths between 500 and 1200 nm. The pulse sequence of this example delivers radiant energy at a higher rate than in the third example because of the shorter inter-pulse interval and the slightly higher energy delivered per pulse.

Home Use Example 5

In a lower setting or combination of operational parameters, an incoherent light applicator device produces pulses with a pulse number of two, a pulse duration of 5 msec, an inter-pulse interval of 350 msec, a total pulse energy of 15 $J/cm^2$, and a spectral distribution of a commercially available flashlamp, including wavelengths between 500 and 1200 nm. The pulse sequence of this example delivers a small amount of energy, at a low rate (e.g., long inter-pulse interval).

Home Use Example 6

A slightly higher setting or combination of operational parameters for an incoherent light applicator device involves pulses with a pulse number of two, a pulse duration of 5 msec, an inter-pulse interval of 300 msec, a total pulse energy of 20 $J/cm^2$, and a spectral distribution of a commercially available flashlamp, including wavelengths between 500 and 1200 nm.

Home Use Example 7

A lower setting or combination of operational parameters for an incoherent light applicator device involves pulses with a pulse number of three, a pulse duration of 5 msec, an inter-pulse interval of 300 msec, a total pulse energy of 20 $J/cm^2$, and a spectral distribution of a commercially available flashlamp, including wavelengths between 500 and 1200 nm.

Home Use Example 8

Another setting or combination of operational parameters for an incoherent light applicator device involves pulses with a pulse number of two, a pulse duration of 7 msec, an inter-pulse interval of 250 msec, a total pulse energy of 20 $J/cm^2$, and a spectral distribution of a commercially available flashlamp, including wavelengths between 500 and 1200 nm.

The devices of FIGS. 1 and 2 may be provided with a band-pass filter for limiting the spectral distribution of the generated light pulses to wavelengths in a given band, for instance, between 700 nm and 900 nm. Alternatively, a low-pass filter may be used for transmitting to target hair fibers only wavelengths less than a predetermined maximum, such as 900 nm, 750 nm, or 550 nm. Alternatively, a high-pass filter may be used for transmitting to target hair fibers only wavelengths greater than a predetermined wavelength such as 430 nm, 610 nm, and 750 nm.

Listed below are a number of exemplary settings or combinations of operational parameters particularly suitable for professional devices. In these examples, the total times of the pulse sequences are determined by the selected numbers of pulses, the selected pulse durations and the selected inter-pulse intervals. The light intensity may be automatically adjusted by the light generating device if necessary to ensure consistency among the listed parameter settings.

Professional Use Example 1

In a setting or combination of operational parameters suitable for professional use, an incoherent light applicator device for hair styling generates pulses with a pulse number of two, a pulse duration of 7 msec, an inter-pulse interval of 150 msec, a total pulse energy of 60 J/cm², and a spectral distribution of a commercially available flashlamp, including wavelengths between 500 and 1200 nm.

Professional Use Example 2

A slightly higher setting or combination of operational parameters for an incoherent light applicator device involves pulses with a pulse number of two, a pulse duration of 7 msec, an inter-pulse interval of 100 msec, a total pulse energy of 60 J/cm², and a spectral distribution of a commercially available flashlamp, including wavelengths between 500 and 1200 nm.

Professional Use Example 3

A lower setting or combination of operational parameters for an incoherent light applicator device involves pulses with a pulse number of two, a pulse duration of 9 msec, an inter-pulse interval of 100 msec, a total pulse energy of 60 J/cm², and a spectral distribution of a commercially available flashlamp, including wavelengths between 500 and 1200 nm.

Professional Use Example 4

A higher setting or combination of operational parameters for an incoherent light applicator device involves pulses with a pulse number of two, a pulse duration of 9 msec, an inter-pulse interval of 100 msec, a total pulse energy of 100 J/cm², and a spectral distribution of a commercially available flashlamp, including wavelengths between 500 and 1200 nm.

Professional Use Example 5

In a relatively low setting or combination of operational parameters for professional use, an incoherent light applicator device produces pulses with a pulse number of two, a pulse duration of 9 msec, an inter-pulse interval of 200 msec, a total pulse energy of 40 J/cm², and a spectral distribution of a commercially available flashlamp, including wavelengths between 500 and 1200 nm.

Professional Use Example 6

A slightly higher setting or combination of operational parameters for an incoherent light applicator device involves pulses with a pulse number of two, a pulse duration of 5 msec, an inter-pulse interval of 150 msec, a total pulse energy of 40 J/cm², and a spectral distribution of a commercially available flashlamp, including wavelengths between 500 and 1200 nm.

Professional Use Example 7

Another higher setting or combination of operational parameters for an incoherent light applicator device involves pulses with a pulse number of two, a pulse duration of 5 msec, an inter-pulse interval of 150 msec, a total pulse energy of 50 J/cm², and a spectral distribution of a commercially available flashlamp, including wavelengths between 500 and 1200 nm.

An incoherent light applicator device for professional use may also be provided with a band-pass filter for limiting the spectral distribution of the generated light pulses to wavelengths in a given band, for instance, between 700 nm and 900 nm. Again, a low-pass filter may be used for transmitting to hair fibers only wavelengths less than a predetermined maximum, such as 900 nm, 750 nm, or 550 nm. Alternatively, a high-pass filter may be used for transmitting to target hair fibers only wavelengths greater than a predetermined wavelength such as 430 nm, 610 nm, and 750 nm.

The light applied to hair fibers by the devices of FIGS. 1 and 2 includes at least one wavelength absorbable by an endogenous chromophore in a person's hair. The endogenous chromophore may be a form of melanin such as pheomelanin or eumelanin. In a more advanced embodiment the light application device may include a setting or control (not shown) for selecting a spectrum or range of wavelengths appropriate to the user's hair color. For instance, for lighter hair, the wavelengths selected encompass one or more natural absorption wavelengths of pheomelanin. For darker hair, the wavelengths selected encompass one or more natural absorption wavelengths of eumelanin. In any event, the devices of FIGS. 1 and 2 may be used, as discussed above, with the application of an exogenous chromophore (dye) to the hair fibers for light absorption purposes.

Although the invention has been described in terms of particular embodiments and applications, one of ordinary skill in the art, in light of this teaching, can generate additional embodiments and modifications without departing from the spirit of or exceeding the scope of the claimed invention. For example, light sources 18 and 42 may take the form of laser sources. In that case, if optical elements 22 and 48 include any filters, those filters are neutral density filters for reducing the intensity of the transmitted radiation. Where light sources 18 and 42 are tunable laser sources, then an additional actuator may be provided for frequency selection purposes. Accordingly, it is to be understood that the drawings and descriptions herein are proffered by way of example to facilitate comprehension of the invention and should not be construed to limit the scope thereof.

What is claimed is:

1. A method for styling hair, comprising:
   applying a light-absorbing composition to protruding hair fibers of an individual;
   generating a predetermined number of pulses of light each having a predetermined electromagnetic spectrum with one or more wavelengths absorbable by said light-absorbing composition;
   directing said pulses of light at least in part towards portions of said protruding hair fibers to which said light absorbing composition has been applied, said pulses having at least one pulse duration and a total energy all predetermined to differentially heat the hair fibers in a region along one side of the hair fibers and thereby effectively vary curvature of the hair fibers in said region owing to absorption of light of said pulses by at least said light-absorbing composition; and
   by virtue of the directing of said pulses of light towards said protruding hair fibers and absorption of light of said pulses by said light-absorbing composition, changing curvature of said hair fibers in said region, without removing more than an incidental number of the hair fibers.

2. The method defined in claim 1 wherein said light-absorbing composition is taken from the group consisting of water and a dye.

3. The method defined in claim 1 wherein said light-absorbing composition is applied uniformly to said hair fibers, the directing of said pulses of light towards said hair fibers including directing said pulses of light differentially to said hair fibers.

4. The method defined in claim 1 wherein said light-absorbing composition is applied differentially to said hair fibers.

5. A method for styling hair, comprising:

generating a predetermined number of pulses of light each having a predetermined electromagnetic spectrum with one or more wavelengths absorbable by hair;

selectively directing said pulses of light towards a selected region along the lengths of a number of protruding hair fibers of an individual, said pulses having at least one pulse duration and a total energy all predetermined to differentially heat the hair fibers in said region along one side of the hair fibers and thereby effectively vary curvature of the hair fibers in said region of the hair fibers, owing to absorption of light of said pulses by the hair fibers in said region; and by virtue of the directing of said pulses of light towards said hair fibers and absorption of light of said pulses by said hair fibers, changing the curvature of said hair fibers in said region, without removing more than an incidental number of the hair fibers.

6. A method for hair treatment, comprising:

generating a predetermined number of pulses of light each having a predetermined electromagnetic spectrum with one or more wavelengths absorbable by hair;

directing said pulses of light towards protruding hair fibers of an individual, said pulses having at least one pulse duration and a total energy all predetermined to effectively vary a characteristic of the hair fibers owing to absorption of light of said pulses by the hair fibers;

by virtue of the directing of said pulses of light towards said hair fibers and absorption of light of said pulses by said hair fibers, changing at least one selected characteristic of said hair fibers, said one selected characteristic being hair length, the directing of said pulses of light towards said hair fibers including directing said pulses of light towards end segments of hair fibers; and automatically detecting free ends of said hair fibers, the directing of said pulses of light towards said hair fibers including directing said pulses of light towards said hair fibers at a given distance from the free ends of said hair fibers.

7. A hair styling method comprising:

generating electromagnetic radiation having a predetermined spectral composition and a predetermined intensity in a predetermined number of light pulses each having a predetermined duration, said light pulses having a predetermined total energy; and selectively directing said light pulses towards hair fibers protruding from a skin surface so that the light pulses do not remove or sever without removing more than an incidental number of the hair fibers and so that the generated light pulses are absorbed by the hair fibers, above or outside of a person's skin, to thereby affect hair fiber thickness, the directing of said pulses of light towards said hair fibers including directing said pulses of light along the lengths of said hair fibers, to split said hair fibers longitudinally, thereby increasing the numbers of said hair fibers and reducing fiber thickness.

8. The method defined in claim 7 wherein the directing of said light pulses includes directing said light pulses away from said skin surface.

9. A method for hair treatment, comprising:

applying a light-activated adhesive composition to protruding hair fibers of an individual;

generating a predetermined number of pulses of light each having a predetermined electromagnetic spectrum with one or more wavelengths absorbable by at least said light-activated adhesive composition; and directing said pulses of light along at least a portion of the lengths of said hair fibers after the applying of said light-activated adhesive composition to said hair fibers, at least in part to activate said adhesive composition to couple fiber sections to one another and to thereby increase fiber thickness.

* * * * *